(12) United States Patent
Valdez et al.

(10) Patent No.: US 9,791,463 B2
(45) Date of Patent: Oct. 17, 2017

(54) METHODS FOR THE SELECTIVE DETECTION OF ALKYNE-PRESENTING MOLECULES AND RELATED COMPOSITIONS AND SYSTEMS

(71) Applicant: Lawrence Livermore National Security, LLC, Livermore, CA (US)

(72) Inventors: Carlos A. Valdez, San Ramon, CA (US); Alexander K. Vu, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 706 days.

(21) Appl. No.: 14/201,530

(22) Filed: Mar. 7, 2014

(65) Prior Publication Data

US 2014/0273274 A1    Sep. 18, 2014

Related U.S. Application Data

(60) Provisional application No. 61/790,019, filed on Mar. 15, 2013, provisional application No. 61/790,393, filed on Mar. 15, 2013, provisional application No. 61/790,757, filed on Mar. 15, 2013.

(51) Int. Cl.
| | | |
|---|---|---|
| *G01N 33/00* | (2006.01) | |
| *G01N 33/74* | (2006.01) | |
| *G01N 33/53* | (2006.01) | |
| *C08F 112/08* | (2006.01) | |
| *G01N 33/18* | (2006.01) | |

(52) U.S. Cl.
CPC .......... *G01N 33/743* (2013.01); *C08F 112/08* (2013.01); *G01N 33/1826* (2013.01); *G01N 33/5308* (2013.01)

(58) Field of Classification Search
CPC .................................................... G01N 33/743
USPC ........................................................ 436/172
See application file for complete search history.

(56) References Cited

U.S. PATENT DOCUMENTS

2008/0241856 A1\* 10/2008 Wong .................. G01N 1/30
                                                                 435/7.1
2009/0297609 A1    12/2009  Soichet et al.
2012/0226019 A1     9/2012  Aucagne et al.

FOREIGN PATENT DOCUMENTS

GB            1325912 A        8/1973

OTHER PUBLICATIONS

Haiyu Tian, Junhong Qian, Hongyan Bai, Qian Sun, Lingyi Zhang, Weibing Zhang "Micelle-induced multiple performance improvement of fluorescent probes for H2S detection" Analytica Chimica Acta 768 (2013) 136-142.\*

(Continued)

*Primary Examiner* — Christopher A Hixson
*Assistant Examiner* — Emily Berkeley
(74) *Attorney, Agent, or Firm* — Steinfl + Bruno, LLP

(57) ABSTRACT

Provided herein are methods for selectively detecting an alkyne-presenting molecule in a sample and related detection reagents, compositions, methods and systems. The methods include contacting a detection reagent with the sample for a time and under a condition to allow binding of the detection reagent to the one or more alkyne-presenting molecules possibly present in the matrix to the detection reagent. The detection reagent includes an organic label moiety presenting an azide group. The binding of the azide group to the alkyne-presenting molecules results in emission of a signal from the organic label moiety.

8 Claims, 12 Drawing Sheets

(56) References Cited

OTHER PUBLICATIONS

JennIfer A. Field, Larry B. Barber, E. MIchael Thurman, Billy L. Moore, David L. Lawrence, and DavId A. Peake "Fate of Alkylbenzenesulfonates and Dialkyltetralinsulfonates in Sewage-Contaminated Groundwater" Environ. Sci. Technol. 1992, 26, 1140-1148.*
Restriction Requirement for U.S. Appl. No. 14/201,545, filed Mar. 7, 2014 on behalf of Carlos A. Valdez. dated Oct. 7, 2015. 7 pages.
Non-Final Office Action for U.S. Appl. No. 14/201,545, filed Mar. 7, 2014 on behalf of Carlos A. Valdez. dated Dec. 17, 2015. 13 pages.
Final Office Action for U.S. Appl. No. 14/201,545, filed Mar. 7, 2014 on behalf of Carlos A. Valdez. dated Jul. 14, 2016. 14 pages.
Restriction Requirement for U.S. Appl. No. 14/201,480, filed Mar. 7, 2014 on behalf of Carlos A. Valdez. dated Sep. 9, 2016. 10 pages.
Balli et al. "Synthese von 1-Athyl-2-azido-6-X-chinolinium-fluoroboraten" Helvetica Chimica Acta; 1970; vol. 53; No. 7; pp. 1903-1912—English Abstract Only + Full German text.
Sezer et al. "Transdiazotization of Acylacetaldehydes in Neutral-to-Acidic Medium. A Direct Approach to the Synthesis of α-Diazo-β-oxoaldehydes)" Helvetica Chimica Acta; 1994; vol. 77; pp. 2323-2334.
Szanti-Pinter et al. "Synthesis of ferrocene-labelled steroid derivatives via homogenous catalytic methods" Journal of Organometallic Chemistry; 2012; vol. 718; pp. 105-107.
Szanti-Pinter et al. "Synthesis of steroid-ferrocene conjugates of steroidal 17-carboxamides via a palladium-catalyzed aminocarbonylation—Copper-catalyzed azide-alkyne cycloaddition reaction sequence" Steroids; 2011; vol. 76; pp. 1377-1382.
Upton et al. "Synthesis of ferrocene-functionalized monomers for biodegradable polymer formation" Inorg. Chem. Front.; 2014; vol. 1; pp. 271-277.
Van Berkel, G.J., et al. "Deprivation for Electrospray Ionization Mass Spectrometry. 3. Electrochemically Ionizable Derivatives." Anal. Chem., vol. 70, pp. 1544-1554. 1998.
Higashi, T. et al. "Derivatization of neutral steroids to enhance their detection characteristics in liquid chromatography-mass spectrometry." Anal Bioanal Chem., vol. 378, pp. 872-882. 2004.
Ternes, T.A. et al. "Determination of Estrogens in Sludge and Sediments by Liquid Extraction and GC/MS/MS." Anal. Chem., vol. 74, pp. 3498-3504. 2002.
Thompson, A. S. et al. "Direct Conversion of Activated Alcohols to Azides Using Diphenyl Phosphorazidate. A Practical Alternative to Mitsunobu Conditions." J. Org. Chem., vol. 58, pp. 5886-5888. 1993.
Cassidy, M.P. et al. "Practical Synthesis of Amides from In Situ Generated Copper (I) Acetylides and Sulfonyl Azides." Angew. Chem. Int. Ed., vol. 45, pp. 3154-3157. 2006.
Danheiser, R.L. et al. "An Improved Method for the Synthesis of a α-Diazo Ketones." J. Org. Chem., vol. 55(6), pp. 1959-1964. 1990.
Shved, N. et al. "Environmentally Relevant Concentrations of 17α-Ethinylestradiol (EE2) Interfere With the Growth Hormone (GH)/Insulin-Like Growth Factor (IGF)-I Systems in Developing Bony Fish." Toxicological Science, vol. 106(1), pp. 93-102. 2008.
Seiwert, B. and Karst, U. "Ferrocene-based derivatization in analytical chemistry." Anal Bioanal Chem., vol. 390, pp. 181-200. 2008.
Fukuzawa, S. et al. "ClickFerrophos: New Chiral Ferrocenyl Phosphine Ligands Synthesized by Click Chemistry and the Use of Their Metal Complexes as Catalysts for Asymmetric Hyrdogenation and Allylic Substitution." Organic Letter, vol. 9(26), pp. 5557-5560. 2007.
Quirke, J.M.E. et al. "Ferrocene-Based Electroactive Derivatizing Reagents for the Rapid Selective Screening of Alcohols and Phenols in Natural Product Mixtures Using Electrospray-Tandem Mass Spectrometry." J. Nat. Prod., vol. 63, pp. 230-237. 2000.
Kuch, H. M. et al. "Determination of Endocrine-Disrupting Phenolic Compounds and Estrogens in Surface and Drinking Water by HRGC-(NCI)-MS in the Picogram per Liter Range." Environ. Sci. Technol. vol. 35, pp. 3201-3206. 2001.
Barnett, S.M. et al. Surface-Enhanced Raman Scattering Spectroscopic Study of 17α Ethinylestradiol on Silver Colloid and in Glass-Deposited Ag—I 7a-Ethinylestradiol Film. Anal.Chem., vol. 66, pp. 1762-1765. 1994.
Van Berkel, G.J. et al. "Preforming Ions in Solution via Charge-Transfer Complexation for Analysis by Electrospray Ionization Mass Spectrometry." Anal. Chem., vol. 63 (18), pp. 2064-2068. 1991.
Sletten, E.M., et al., "Bioorthogonal chemistry: fishing for selectivity in a sea of functionality" Angew Chem Int Ed Engl (2009) 48, 38, 6974-6998.
Prescher, J.A., et al., "Chemical remodelling of cell surfaces in living animals" Nature (2004) 430, 7002, 873-877.
Sawa, M., et al., "Glycoproteomic probes for fluorescent imaging of fucosylated glycans in vivo" Proc Natl Acad Sci U S A (2006) 103, 33, 12371-12376.
Baskin, J.M., et al., "Copper-free click chemistry for dynamic in vivo imaging" Proc Natl Acad Sci U S A (2007) 104, 43, 16793-16797.
Zhang, L., et al., "Ruthenium-catalyzed cycloaddition of alkynes and organic azides" J Am Chem Soc (2005) 127, 46, 15998-15999.
Horiba, J.Y., "A guide to recording fluorescence quantum yields" (2002) Stanmore.
Trupp, S. et al., "A fluorescent water-soluble naphthalimides-based receptor for saccharides with highest sensitivity in the physiological pH range" Org. Biomol. Chem. (2006) 4, 2965-2968.
Schneider, C. et al., "Direct sub-ppt detection of the endocrine disruptor ethinylestradiol in water with a chemiluminescence enzyme-linked immunosorbent assay" Anal. Chim. Acta (2005) 551, 92-97.
Sivakumar, K. et al., "A Fluorogenic 1,3-Dipolar Cycloaddition Reaction of 3-Azidocoumarins and Acetylenes" Org. Lett. (2004) 6, 4603-4606.
Rostovtsev, V. V. et al., "A Stepwise Huisgen Cycloaddition Process: Copper(I)-Catalyzed Regioselective "Ligation" of azides and terminal alkynes" Angew. Chem. Int. Ed. Engl. (2002) 41, 2596-2599.
Tornoe, C. et al., "Peptidotriazoles on Solid Phase: [1,2,3]-triazoles by Regiospecific Copper(I)-Catalyzed 1,3-Dipolar Cycloadditions of Terminal Alkynes to Azides" J. Org. Chem. (2002) 67, 3057-3064.
Fery-Forgues, S., et al., "Are Fluorescence Quantum Yields So Tricky to Measure? A Demonstration Using Familiar Stationery Products" J. Chem. Ed. (1999) 76, 1260-1264.
Snyder, S. A. et al., "Analytical Methods for Detection of Selected Estrogenic Compounds in Aqueous Mixtures" Environ. Sci. Technol. (1999) 33, 2814-2820.
Colborn, T. "Building Scientific Consensus on Endocrine Disruptors" Environmental Toxicology and Chemistry (1998) 17, 1-2.
Smith, P. A. S., et al., "Kinetic Evidence for the Formation of Azene (Electron-Defficient Nitrogen) Intermediates from Aryl Azides" J. Am. Chem. Soc. (1961) 84, 480-485.
Melhuish, W. H. "Quantum Efficiencies of Fuorescence Organic Substances: Effect of Solvent and Concentration of the Fluorescent Solute" J. Phys. Chem. (1960) 65, 229-235.
Richardson, S.D., "Water Analysis: Emerging Contaminants and Current Issues" Anal. Chem. (2009) 81, 4645-4677.
Hanaoka, K., et al., "Design and Synthesis of a Highly Sensitive Off-On Fluorescent Chermosensor for Zinc Ions Utilizing Internal Charge Transfer" Chem. Eur. J. (2010), 16, 568-572.
Martinez, N.A. et al., "Modified Paramagnetic Beads in a Microfluidic System for the Determination of Ethinylestradiol (EE2) in River Water Samples" Biosensors and Bioelectronics, 25 (2010) 1376-1381.
Hannah, R., et al., "Exposure Assessment of 17α-Ethinylestradiol in Surface Waters of the United States and Europe" Environmental Toxicology and Chemistry (2009) 28, 12, 2725-2732.
Non-Final Office Action for U.S. Appl. No. 14/201,545, filed Mar. 7, 2014 on behalf of Carlos A. Valdez. dated Apr. 6, 2017. 13 pages.
Sigma-Aldrich, Excerpt from "Resins for Solid-Phase Synthesis" retrieved from http://web.archive.org/web/20120629084629/http://

(56) References Cited

OTHER PUBLICATIONS www.sigmaaldrich.com/chemistry/drug-discovery/resin-explorer/solid-phase-resins.html on Jan. 12, 2017. 1 page.
7 Fluka, Resins for solid-phase Peptide Synthesis, vol. 3, No. 4, 2003, 32 pages.

\* cited by examiner

METHODS FOR THE SELECTIVE DETECTION OF ALKYNE-PRESENTING MOLECULES AND RELATED COMPOSITIONS AND SYSTEMS

CROSS REFERENCE TO RELATED APPLICATIONS

The present application claims priority to U.S. Provisional Application 61/790,019 entitled "Methods for The Selective Detection of Alkyne-Presenting Molecules and Related Compositions and Systems" filed on Mar. 15, 2013, to U.S. Provisional Application 61/790,393 entitled "Methods for The Selective Detection of Alkyne-Presenting Molecules and Related Compositions and Systems" filed on Mar. 15, 2013, and to U.S. Provisional Application 61/790,757 entitled "Methods for The Selective Sequestration of Alkyne-Presenting Molecules and Related Compositions and Systems" filed on Mar. 15, 2013, each of which is herein incorporated by reference in their entirety. This application may be related to U.S. Non-Provisional application Ser. No. 14/201,480 and entitled "Methods for The Selective Detection of Alkyne-Presenting Molecules and Related Compositions and Systems" filed on Mar. 7, 2014 and to U.S. Non-Provisional application Ser. No. 14/201,545 and entitled "Methods for The Selective Sequestration of Alkyne-Presenting Molecules and Related Compositions and Systems" filed on Mar. 7, 2014, each of which is herein incorporated by reference in their entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to methods for detection of alkyne-presenting molecules, and in particular 17α-ethinylestradiol, and related compositions and systems.

BACKGROUND

Detection of alkyne-presenting molecules, such as 17α-ethinylestradiol and other steroid-based contaminants, in the environment, particularly in water systems, has become an issue of utmost importance due to the toxic effects exerted by these chemical species in biological systems even at very low concentrations.

However, specific and selective detection of those compounds can be challenging also in view of the fact that several synthetic and natural chemicals possess the ability to mimic hormones and as such are able to interfere or disrupt hormonal homeostasis in biological systems.

Accordingly, despite the fact that several methods and systems for detection of alkyne-presenting molecules, and in particular 17α-ethinylestradiol, are available, performance of an accurate and selective detection remains challenging.

SUMMARY

Described herein are methods and related compositions and systems that in some embodiments can be used in the selective detection, and quantification of steroids, and in particular, the selective detection, and quantification of alkyne presenting molecules, and in particular 17α-ethinylestradiol.

According to a first aspect, a method and system for selectively detecting an alkyne-presenting molecule, and in particular 17α-ethinylestradiol, in an unprepared sample is described, the method comprising: contacting the unprepared sample with a detection reagent for a time and under a condition allowing binding of the detection reagent to one or more alkyne presenting molecules in the sample wherein the detection reagent comprises a label organic moiety presenting an azide group, wherein binding of detection reagent to one or more alkyne presenting molecule comprises binding of the azide group to an alkyne group of the alkyne-presenting molecules and wherein binding of the azide group to the one or more alkyne-presenting molecules results in emission of a signal. In some embodiments, the organic label moiety can comprises a fluorescent or pre-fluorescent moiety. The system comprises at least one of one or more detection reagents herein described, reagents for the alkyne group azide group reaction and/or a copper(I) source for the simultaneous, combined, or sequential use in the method herein described.

According to a second aspect, a detection reagent is described, the detection reagent comprising: one or more label organic moieties, the label organic moieties each presenting an azide group; wherein the label organic moieties are adapted to produce a signal when the detection reagent is bound to one or more alkyne-presenting molecules, and in particular 17α-ethinylestradiol molecules. In some embodiments, the one or more label organic moieties are fluorescent or pre-fluorescent moieties.

The methods and related compositions and systems described herein in several embodiments allow the selective fluorescence detection of alkyne-presenting molecules, and in particular 17α-ethinylestradiol, in unprepared aqueous and organic samples.

The methods and related compositions and systems described herein in several embodiments can be used, for example, for the detection and analysis of the alkyne-presenting molecules, such as contraceptive pill's active ingredient 17-α-ethinylestradiol (EE2), in various unprepared water matrices and organic media using the technique of fluorescence spectroscopy. Furthermore, application of these methods and related compositions and systems can be extended, for example, to EE2 detection in blood and urine samples that can become important if monitoring systems are to be developed for individuals consuming the drug.

The methods and related compositions and systems described herein in several embodiments can be used, for example, for the detection and/or removal of the contraceptive pill's active ingredient 17-α-ethinylestradiol (EE2) from various water matrices and organic media using the Cu(I)-catalyzed 1,3-dipolar cycloaddition reaction commonly known as "click chemistry". Furthermore, application of these methods and related compositions and systems can be extended to the building of purification devices that possess the azido-functionality and thus are able to directly interact with alkyne-presenting molecules such as EE2 without the need for sample preparation.

The details of one or more embodiments of the disclosure are set forth in the accompanying drawings and the description below. Other features and objects will be apparent to a skilled person from the description and drawings, and from the claims.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 3, panel A shows a schematic of a general scheme depicting an exemplary naphthalimide-based probe according to embodiments herein described highlighting its three main sections along with their properties/functions. FIG. 3, panel B shows a schematic of a structure of an exemplary EE2-probe adduct according to embodiments herein described that can result from the cycloaddition reaction an exemplary naphthalimide-based probe and EE2 exhibiting a 20-fold increase in fluorescence relative to the starting probe.

DETAILED DESCRIPTION

Figure 1:
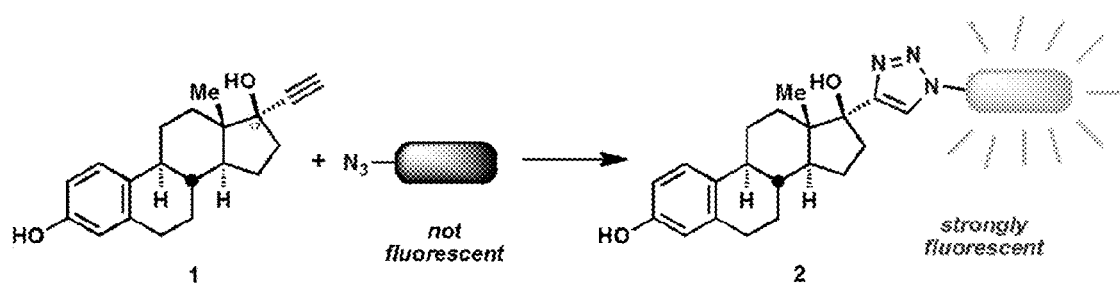
FIG. 1 shows the a schematic of structure of the contraceptive 17α-ethinylestradiol (EE2) and the reaction between EE2 and a fluorogenic probe bearing an azide functionality that results in the formation of a strongly fluorescent triazole adduct according to embodiments herein described.

Described herein are methods and related compositions and systems that in some embodiments can be used in the selective detection, and/or quantification of alkyne-presenting molecules, and in particular, the selective detection, and/or quantification of alkyne presenting molecule, and in particular 17α-ethinylestradiol.

The term "alkyne presenting molecule" as used herein indicates a molecule presenting a alkyne group for binding. The term "present" as used herein with reference to a compound or functional group indicates attachment performed to maintain the chemical reactivity of the compound or functional group as attached. Accordingly, an alkyne group presented on a molecule, is able to perform under the appropriate conditions the one or more chemical reactions that chemically characterize the alkyne group including click chemistry. In particular, an alkyne group can be included in an alkyne presenting molecule in any position and configuration as long as the alkyne group is presented in the molecule for binding or be subjected to other reactions.

In some embodiments herein described, the alkyne presenting molecule comprises a terminal alkyne. Exemplary molecule wherein the alkyne presenting molecule comprises a terminal alkyne include, for example, 17α-ethinylestradiol, acetylene, propyne, norethynodrel, rasagiline, and others identifiable to a skilled person.

In some embodiments herein described the alkyne presenting molecule comprises an internal alkyne group. Exemplary molecule wherein the alkyne presenting molecule comprises an internal alkyne include, for example, terbinafine, cicutoxin, oenanthotoxin, falcarinol, efavirenz, calicheamicin, tariric acid, and others identifiable to a skilled person.

In particular, in some embodiments, the methods and related compositions and systems can be used in the selective detection of alkyne-presenting molecules, and in particular 17α-ethinylestradiol, in unprepared aqueous and organic samples.

The terms "detect" or "detection" as used herein indicates the determination of the existence, presence or fact of a target in a limited portion of space, including but not limited to a sample, a reaction mixture, or other limited portion of space identifiable to a skilled person upon a reading of the present disclosure. The detection can be quantitative or qualitative. A detection is "quantitative" when it refers to, relates to, or involves the measurement of quantity or amount of the target or signal (also referred as quantitation), which includes but is not limited to any analysis designed to determine the amounts or proportions of the target or signal. A detection is "qualitative" when it refers to, relates to, or involves identification of a quality or kind of the target or signal in terms of relative abundance to another target or signal, which is not quantified.

The term "signal", as used herein, refers to a detectable output associated with a particular target of interest and can be used to qualitatively or quantitatively detect the target. In particular, exemplary signals can include, for example, fluorescence, phosphorescence, chemiluminescence, radioactivity, magnetism (e.g. as in Nuclear Magnetic Resonance spectroscopy) and others identifiable to a skilled person.

The term "sample" as used herein indicates a limited quantity of something that is indicative of a larger quantity of that something, including but not limited to solids and/or fluids from a biological environment, specimen, cultures, tissues, or portions thereof. In some embodiments, the sample can be an aqueous or organic solution containing a particular substance of interest. Exemplary samples in the sense of the current disclosure include an environment sample collected from water, soil, air or the outer space, samples collected from a surface of a facility, equipment or system, food or pharmaceutical preparation, including, for example, blood, urine, drinking water, agricultural irrigation water and others identifiable to a skilled person upon a reading of the present disclosure.

In particular, in some embodiments, the sample is an unprepared sample. The term "unprepared sample" as used herein refers to a sample that has not been subjected to sample preparation, wherein the term "sample preparation" refers to the way a sample is treated prior to its analysis to introduce an azide (—$N_3$) group or alkyne group into a molecule (e.g., by incorporating an azide- or alkyne-bearing sugar or amino acid into a biomolecule; see, e.g. [Ref 1-4]) for binding to a detection reagent through "click chemistry" as described herein, and other sample preparations that would be apparent to a skilled person upon a reading of the present disclosure. In particular, in some instances absence of sample preparation in the sense of the present disclosure can result in a method wherein reacting an azide presenting molecule with the alkyne presenting molecule is performed without any information beforehand as to the quantity, concentration, or chemical reactivity of the compound presenting the alkyne group, and possibly also the chemical composition of the medium when the reaction is expected to occur.

Accordingly, according to some embodiments of the disclosure, the amount of azide or alkyne in a molecule to be detected, and thus the amount of molecule to be detected (e.g. an alkyne-presenting molecule) is not known beforehand in the unprepared samples herein described.

In particular, in some embodiments, the selective detection of alkyne-presenting molecules, comprised in an unprepared sample: contacting the unprepared sample with a detection reagent for a time and under a condition so as to bind the one or more alkyne-presenting molecules in the sample wherein the detection reagent comprises a label organic moiety presenting an azide group and wherein binding of the azide group to the one or more alkyne-presenting molecules results in emission of a signal.

In embodiments in which the alkyne is a terminal alkyne, detection according to embodiments herein described can be performed by contacting the unprepared sample with a label organic moiety presenting an azide group to allow reaction of the alkyne group with the azide group through click chemistry. In some of those embodiments, the reaction can be performed as herein described at room temperature or up to temperatures of between approximately 40-60° C. or of up to temperatures of 100° C. A skilled person can choose the temperature by considering, for example, the thermal stability of the label organic moiety presenting an azide group (e.g. if the label organic moiety presenting an azide group is an aryl azide, the temperature can be kept below 60° C. or other temperature suitable to prevent thermal decomposition of the label organic moiety presenting an azide). In particular, in those embodiments in which the alkyne is an internal alkyne and the temperature is to be maintained below approximately 60° C., a catalysts such as a ruthenium-based catalyst (e.g., Cp*RuCl(PPh$_3$)$_2$) can be used in place of Cu(I) to perform the reaction (see, e.g., [Ref 5]). In addition, in those embodiments in which the alkyne is a terminal alkyne, the amount of Cu(I) as herein described can be 5-20 mol % relative to the alkyne component or up to 50 mol % or up to stoichiometric amounts. In addition, in those embodiments in which the alkyne is a terminal alkyne, the amount of ascorbic acid used as herein described can be in excess amounts. In particular, in those embodiments in which the alkyne is a terminal alkyne, the reaction is expected to allow detection of alkyne presenting molecule at least nanomolar levels and possibly picomolar levels.

In embodiments in which the alkyne is an internal alkyne, detection according to embodiments herein described can be performed by contacting alkyne presenting molecule with a label organic moiety presenting an azide group to allow reaction of the alkyne group with the azide group to perform click chemistry. In some of those embodiments, the reaction can be performed at to temperatures of between approximately 40-60° C. or of up to temperatures of 100° C. or higher. A skilled person can choose the temperature by considering, for example, the thermal stability of the label organic moiety presenting an azide group (e.g. if the label organic moiety presenting an azide group is an aryl azide, the temperature can be kept below 60° C. or other temperature suitable to prevent thermal decomposition of the label organic moiety presenting an azide; or if the label organic moiety presenting an azide group is an alkyl azide, the temperature can be above 100° C. and in particular at a temperature above 100° C. suitable to prevent thermal decomposition of the label organic moiety presenting an azide). In particular, in those embodiments in which the alkyne is an internal alkyne and the temperature is to be maintained below approximately 60° C., a catalysts such as a ruthenium-based catalyst (e.g., Cp*RuCl(PPh$_3$)$_2$) can be used in place of Cu(I) to perform the reaction (see, e.g., [Ref 5]). In addition, in those embodiments in which the alkyne is an internal alkyne, the amount of Cu(I) as herein described can be 5-20 mol % relative to the alkyne component or up to 50 mol % or up to stoichiometric amounts. In addition, in those embodiments in which the alkyne is an internal alkyne, the amount of ascorbic acid used as herein described can be in excess amounts. In particular, in those embodiments in which the alkyne is an internal alkyne, the reaction is expected to allow detection of alkyne presenting molecule at least nanomolar levels and possibly picomolar levels.

The term "label", as in "label organic moiety", as used herein as component of an organic molecule refers to a moiety capable of detection, including but not limited to radioactive isotopes, fluorophores, chemiluminescent dyes, chromophores, enzymes, enzymes substrates, enzyme cofactors, enzyme inhibitors, dyes, lanthanide complexes, and the like that are identifiable by a skilled person.

In some embodiments, the label organic moiety is configured to produce a fluorescent signal when bound to the one or more 17α-ethinylestradiol molecules present in the sample.

In particular, in some embodiments, the label organic moiety is adapted to produce a signal when the detection reagent is bound to the one or more 17α-ethinylestradiol molecules present in the sample by comprising a fluorescent or pre-fluorescent moiety.

The term "fluorescent", as used herein, refers to a moiety capable of exhibiting the phenomena of fluorescence when irradiated with light. The term "pre-fluorescent", as used herein, refers to a moiety that is not fluorescent until it is structurally altered. In particular, in some embodiments, the structural alteration comprises one or more functional groups on the pre-fluorescent moiety reacting to provide a new moiety that is structurally different than the original pre-fluorescent moiety and resulting in the moiety now being fluorescent. In particular, in some embodiments, the fluorescent moieties emit fluorescence at wavelengths between 250-600 nm. In other embodiments, the fluorescent molecule emits fluorescence at wavelengths above 800 nm.

Figure 2:
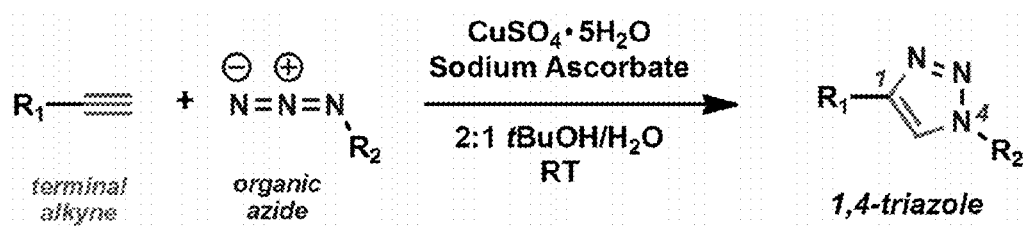
FIG. 2 shows a schematic of The Cu(I)-catalyzed Azide-Alkyne Dipolar Cycloaddition reaction (Click chemistry). Note that the product is a 1,4-substituted triazole ring joining species $R_1$ and $R_2$.

In some exemplary embodiments, detection reagents as herein described can become strongly fluorescent upon covalently binding to an alkyne-presenting molecule (e.g. 17α-ethinylestradiol; see Compound 2 in FIG. 1) in the methods for selective detection of alkyne-presenting molecules, and in particular 17α-ethinylestradiol, herein described. The exemplary method is based on the Copper (I)-catalyzed azide-alkyne 1,3-dipolar cycloaddition reaction, commonly referred to as Click chemistry or as the Copper-catalyzed Hüisgen Cycloaddition. The Hüisgen cycloaddition is a reaction that was discovered in 1967 by Rolph Hüisgen and it entails the fusion of organic azides and terminal alkynes to furnish triazole-containing products. In the present disclosure, reference is often made to the Cu(I)-catalyzed version (termed CuAAC for Cu(I)-catalyzed Azide-Alkyne Cycloaddition) as exemplary click chemistry reaction (FIG. 2) Additional click chemistry reactions can be applied as will be understood by a skilled person. In the illustration of FIG. 2, the reaction involves the 1,3-dipolar cycloaddition of organic azides with terminal alkynes to deliver exclusively 1,4-substituted triazole products. In contrast, the original Hüisgen cycloaddition reaction always yields two products, the 1,5- and the 1,4-substituted triazoles in more or less equal amounts depending on steric factors.

In some embodiments, wherein the CuAAC reaction is used, catalysis by Cu(I) ions can increase the rate of the cycloaddition by $10^7$, making it conveniently fast at or below room temperature. In those embodiments, the reaction is typically not significantly affected by the steric and electronic properties of the groups attached to the azide or alkyne. In particular in some of those embodiments, the reaction can proceed in many protic and aprotic solvents, including water, and is unaffected by most organic and inorganic functional groups, therefore all but eliminating the need for protective group chemistry in the realm of organic synthesis. The 1,2,3-triazole core formed in the process has the advantageous properties of high chemical and thermal stability, a strong dipole moment (4.8-5.6 Debye), aromatic character (UV-active) and hydrogen bond accepting capability. To date, copper is the only metal that stands out as a reliable catalyst for the reaction and several ways of generating the catalytic species (Cu(I)) can be envisioned.

Figure 14:
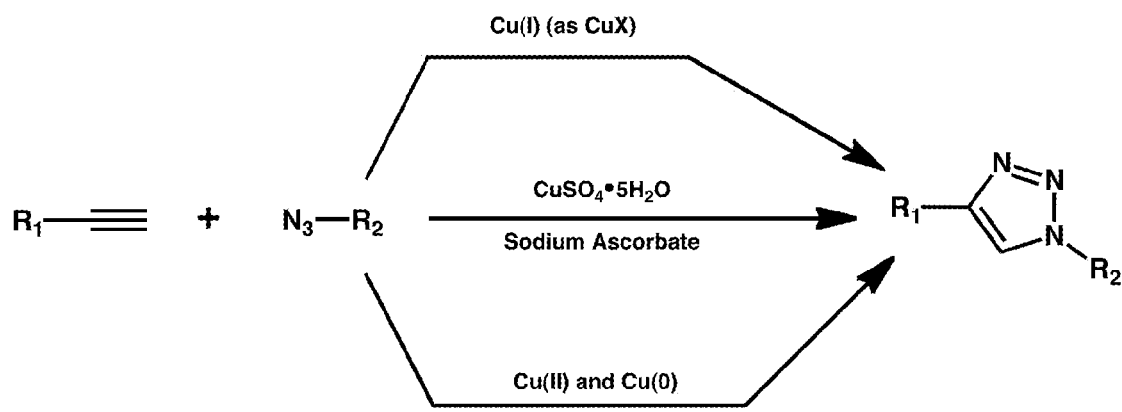
FIG. 14 shows Click chemistry catalyzed by various sources of Cu(I) ions, a) Cu(I) salts; b) Cu(I) from the $CuSO_4$/sodium ascorbate system and c) Cu(I) originating from the Cu(0)/Cu(II) comproportionation reaction as described herein.
Figure 15:
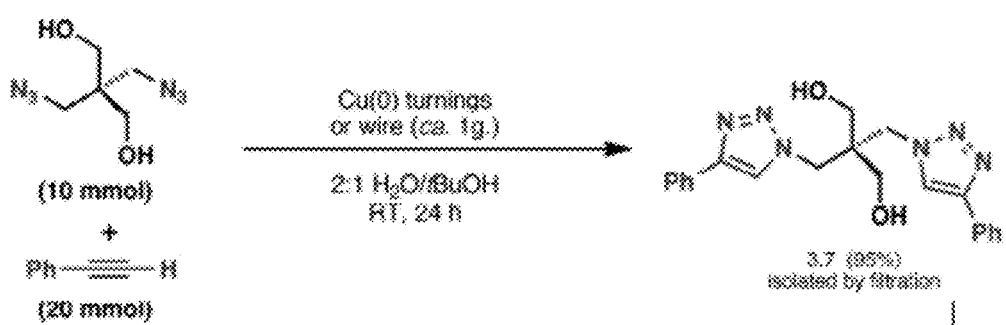
FIG. 15 shows a schematic and image of an exemplary click chemistry reaction using a copper wire as the sole source of catalytic Cu(I) (Fokin group).
Figure 16:
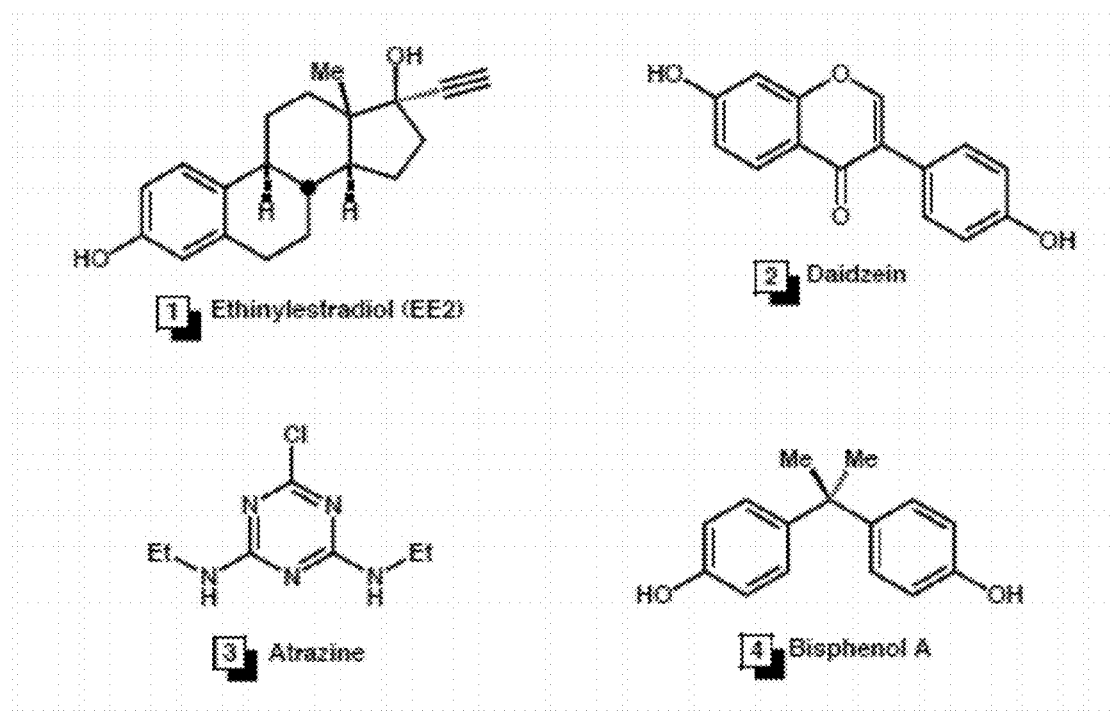
FIG. 16 shows exemplary Endocrine Disrupting Compounds (EDCs).

Therefore, in some embodiments the Cu(I) ions can be provided by direct application of a Cu(I) salt such as CuBr or CuI; the $CuSO_4$/sodium ascorbate system that makes use of the reducing power of the ascorbate to convert Cu(II) into Cu(I) and thus provide the catalytic entity for the cycloaddition to take place. In other embodiments, the Cu(I) species and can be generated based on the comproportionation reaction that elemental copper undergoes. In this reaction, copper metal (Cu(0)) undergoes a reaction in which its Cu(II) oxidation state (always present in small quantities on the outer shell of copper wires, sheets or nanoparticles) to yield the intermediate oxidation state of the metal, namely Cu(I) (FIG. 14). In some of those embodiments only catalytic amounts of Cu(I) are needed to start the cycloaddition reaction, and as such it provides a convenient means to perform the reaction. Thus, the cycloaddition reaction has indeed been shown to work in the presence of a copper wire as illustrated by FIG. 15. In some embodiments, under these conditions, the reaction can be further accelerated by addition of $CuSO_4$ to the solution. In some of those embodiments, the reaction provides a high product yield. In some of those embodiments, the reaction allows use of cheap reaction components. In some of those embodiments, the reaction allows ease of product purification (via vacuum or gravity filtration) and in some of those embodiments, the reaction can be performed with orthogonality.

The term "orthogonality", as used herein, means that only species possessing the terminal alkyne will react with species possessing the azide unit in the presence of Cu(I). Furthermore, this reaction can proceed unaffected by the presence of other functional groups/species (e.g. amines, aldehydes, alcohols, thiols, and additional groups identifiable by a skilled person) and even in the presence of water and oxygen, which eliminates the need for performing it under nitrogen or argon atmospheres. The probes described in this disclosure were born out of this idea, as in the present case Applicants have an analyte (EE2) that possesses a terminal alkyne (at C17) that can be selectively tagged with a species bearing an azide unit.

In particular, in some embodiments, the detection reagent has formula I or II:

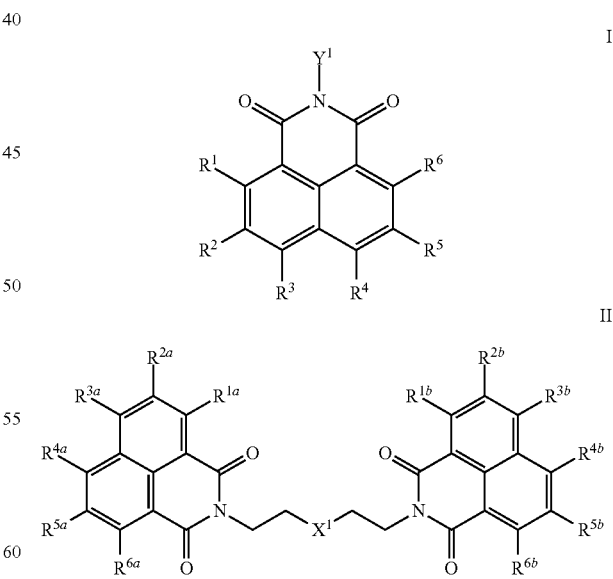

wherein:
$R^1$-$R^6$ are independently selected from the group consisting of H, $N_3$, substituted or unsubstituted $C_1$-$C_8$ alkyl, substituted or unsubstituted amino such that at least one of $R^1$-$R^6$ is $N_3$;

$Y^1$ is selected from the group consisting of H, substituted or unsubstituted $C_1$-$C_8$ alkyl, substituted or unsubstituted aryl or heteroaryl, alkoxy, or polyalkoxy;

$R^{1a}$-$R^{6a}$ and $R^{1b}$-$R^{6b}$ are independently selected from the group consisting of H, $N_3$, substituted or unsubstituted $C_1$-$C_8$ alkyl, substituted or unsubstituted amino, and substituted or unsubstituted oxygen such that at least one of $R^{1a}$-$R^{6a}$ is $N_3$ and at least one of $R^{1b}$-$R^{6b}$ is $N_3$; N and $X^1$ is O, N, NH, N-alkyl, or N-aryl.

In particular, in some embodiments of Formula I, $Y^1$ is selected from the group consisting of formulas III-VI:

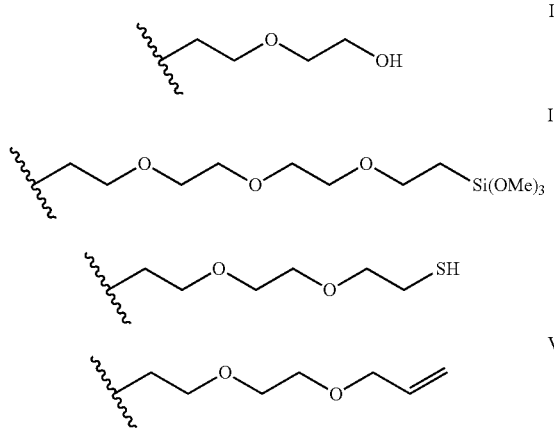

In particular, in some embodiments, the detection reagent has formula VII:

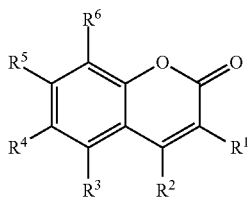

wherein:
$R^1$-$R^6$ are independently selected from the group consisting of H, $N_3$, substituted or unsubstituted $C_1$-$C_8$ alkyl, substituted or unsubstituted amino, and substituted or unsubstituted oxygen such that at least one of $R^1$-$R^6$ is $N_3$.

In some embodiments, the selective detecting of 17α-ethinylestradiol is achieved by measuring the fluorescence of the detection reagent after the contacting. In particular, in some embodiments, the measurement of the fluorescence of the detection reagent can be accomplished with a fluorescence spectrometer and/or with other instruments/techniques identifiable to a skilled person.

In some embodiments, the selective detecting of 17α-ethinylestradiol, or other alkyne-presenting molecules, can also be achieved by the coupling of fluorescence detection with detection by mass spectrometry. In some embodiments, the coupling of fluorescence detection with detection by mass spectrometry can be achieved by performing the contacting with the detection reagents herein described wherein the detection reagents further comprise one or more moieties capable of being detected by mass spectrometry, such as, for example, the ferrocenyl, pyridinium, and other moieties of U.S. Provisional Application 61/790,393 and U.S. Non-Provisional application Ser. No. 14/201,480 and entitled "Methods for The Selective Detection of Alkyne-Presenting Molecules and Related Compositions and Systems" filed on Mar. 7, 2014.

In some embodiments, the moieties capable of being detected by mass spectrometry can be comprised, for example, in the substituents $R^1$-$R^6$ and $R^{1a}$-$R^{6a}$ and $R^{1b}$-$R^{6b}$ of Formulas I, II, and VII by incorporating them into substituents according to methods identifiable to the skilled person. For example, when one of the substituents is a $C_1$-$C_8$ alkyl substituted with an amine, the amine can be coupled to the carbonyl group of ferrocenecarboxylic acid (for example by converting the carboxylic acid to an acid chloride or by using peptide synthesis techniques known to a skilled person).

In some embodiments, the coupling of fluorescence detection with detection by mass spectrometry can allow identification of the detected alkyne-presenting molecule (such as identification of the detected alkyne-presenting molecule as 17α-ethinylestradiol or as another molecule) in addition to its detection.

In some embodiments, the selective detecting of 17α-ethinylestradiol, or other alkyne-presenting molecules, can also be coupled with sequestration of the of 17α-ethinylestradiol, or other alkyne-presenting molecules. In some embodiments, the coupling of the of the detection and sequestration can be achieved by performing the contacting with the detection reagents described herein wherein the detection reagents are further attached to a support of a sequestration reagent such as, for example, the sequestration reagents of U.S. Provisional Application 61/790,757 and U.S. Non-Provisional application Ser. No. 14/201,545 and entitled "Methods for The Selective Sequestration of Alkyne-Presenting Molecules and Related Compositions and Systems" filed on Mar. 7, 2014.

In some embodiments, the detection reagents described herein can be attached to the support of the sequestration reagent through functional groups on the substituents $R^1$-$R^6$ and $R^{1a}$-$R^{6a}$ and $R^{1b}$-$R^{6b}$ of Formulas I, II, and VII by reaction with corresponding functional groups on the support according to methods identifiable to the skilled person. For example, if the support is a polymeric resin (e.g. such as that used in solid phase peptide synthesis) comprising amine groups, then the detection reagents of Formulas I, II, and VII can comprise, for example, $C_1$-$C_8$ alkyl substituted with a carboxylic acid which can be attached to the amine groups of the polymeric resin (for example by converting the carboxylic acid to an acid chloride or by using peptide synthesis techniques known to a skilled person).

In some embodiments, the coupling of detection and sequestration of alkyne-presenting molecules can allow detection of the sequestration. For example, when the detection reagent attached to the sequestration reagent becomes fluorescent only upon covalently bonding to an alkyne-presenting molecule, the sequestration of the alkyne-presenting moiety can be detected by the sequestration reagent becoming fluorescent upon the sequestration of the alkyne-presenting molecule thus indicating that the sequestration has occurred. In some embodiments, the amount of fluorescence can indicate the amount of alkyne-presenting molecule sequestered.

In some embodiments, the systems herein described can be provided in the form of kits of parts. In a kit of parts, one or more detection reagents and copper(I) sources can be comprised in the kit independently. In particular, in some embodiments, the copper(I) source can be a Cu(I) salt (e.g.

CuCl or CuBr). In other embodiments, the copper(I) source can be a Cu(II) salt (e.g. CuSO$_4$) that can be combined with a reducing agent (e.g. ascorbic acid) to provide Cu(I) ions. In other embodiments, the copper(II) source can be a mixture of Cu(0) and Cu(II) sources that can react through comproportionation to provide Cu(II) ions. In other embodiments, the kit of parts can further comprise a reducing agent (e.g. ascorbic acid) to prevent oxidation of the Cu(I) source.

In particular, also described herein is a detection reagent for the selective detection of alkyne-presenting molecules, and in particular 17α-ethinylestradiol. In particular, in some embodiments, the detection reagent comprises one or more label organic moieties, the label organic moieties each presenting an azide group; wherein the label organic moieties are adapted to produce a signal when the detection reagent is bound to one or more alkyne-presenting molecules.

In particular in some embodiments, the detection reagent can have formula VIII or IX:

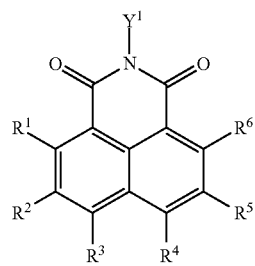

VIII

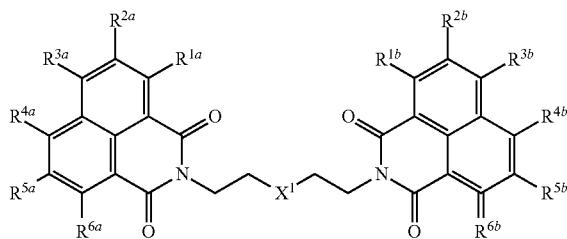

IX wherein;
R$^1$-R$^6$ are independently selected from the group consisting of H, N$_3$, substituted or unsubstituted C$_1$-C$_8$ alkyl, substituted or unsubstituted amino, and substituted and unsubstituted oxygen such that at least one of R$^1$-R$^6$ is N$_3$ Y$^1$ is selected from the group consisting of H, substituted or unsubstituted C$_1$-C$_8$ alkyl, substituted or unsubstituted aryl or heteroaryl, alkoxy, and polyalkoxy groups;

R$^{1a}$-R$^{6a}$ and R$^{1b}$-R$^{6b}$ are independently selected from the group consisting of H, N$_3$, substituted or unsubstituted C$_1$-C$_8$ alkyl, substituted or unsubstituted amino, and substituted or unsubstituted oxygen such that at least one of R$^{1a}$-R$^{6a}$ is N$_3$ and at least one of R$^{1b}$-R$^{6b}$ is N$_3$; and X$^1$ is O, N, NH, N-alkyl, or N-aryl.

In particular, in some embodiments wherein the structure of the detection reagent is according to Formula VIII, Y$^1$ can have a structure according to Formulas X-XIII:

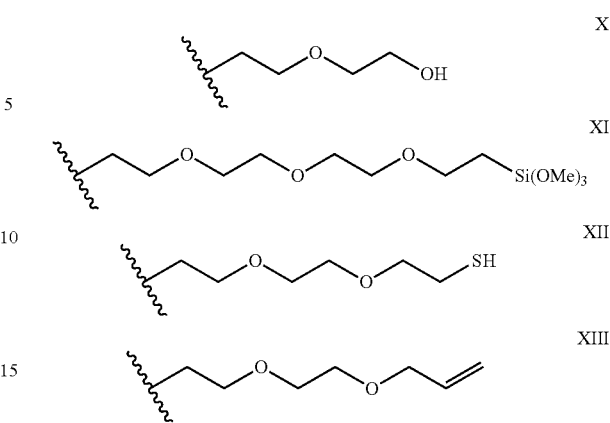

In particular, in some embodiments, the detection reagent can have a structure according to Formula XIV:

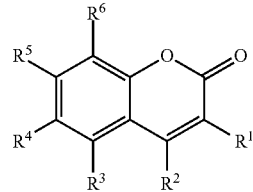

XIV wherein:
R$^1$-R$^6$ are independently selected from the group consisting of H, N$_3$, substituted or unsubstituted C$_1$-C$_8$ alkyl, substituted or unsubstituted amino, and substituted or unsubstituted oxygen such that at least one of R$^1$-R$^6$ is N$_3$ In some embodiments, the detection reagents herein described can further comprise one or more moieties capable of being detected by mass spectrometry, such as, for example, the ferrocenyl, pyridinium, and other moieties of U.S. Provisional Application 61/790,393 and U.S. Non-Provisional application Ser. No. 14/201,480 and entitled "Methods for The Selective Detection of Alkyne-Presenting Molecules and Related Compositions and Systems" filed on Mar. 7, 2014.

In some embodiments, the moieties capable of being detected by mass spectrometry can be comprised, for example, in the substituents R$^1$-R$^6$ and R$^{1a}$-R$^{6a}$ and R$^{1b}$-R$^{6b}$ of Formulas I, II, and VII by incorporating them into the substituents according to methods identifiable to the skilled person. For example, when one of the substituents is a C$_1$-C$_8$ alkyl substituted with an amine, the amine can be coupled to the carbonyl group of ferrocenecarboxylic acid (for example by converting the carboxylic acid to an acid chloride or by using peptide synthesis techniques known to a skilled person).

In some embodiments, the detection reagents herein described can be attached to a support of a sequestration reagent such as, for example, the sequestration reagents of U.S. Provisional Application 61/790,757 and U.S. Non-Provisional application Ser. No. 14/201,545 and entitled "Methods for The Selective Sequestration of Alkyne-Presenting Molecules and Related Compositions and Systems" filed on Mar. 7, 2014.

In some embodiments, the detection reagents described herein can be attached to the support of the sequestration reagent through functional groups on the substituents $R^1$-$R^6$ and $R^{1a}$-$R^{6a}$ and $R^{1b}$-$R^{6b}$ of Formulas I, II, and VII by reaction with corresponding functional groups on the support according to methods identifiable to the skilled person. For example, if the support is a polymeric resin (e.g. such as that used in solid phase peptide synthesis) comprising amine groups, then the detection reagents of Formulas I, II, and VII can comprise, for example, $C_1$-$C_8$ alkyl substituted with a carboxylic acid which can be attached to the amine groups of the polymeric resin (or example by converting the carboxylic acid to an acid chloride or by using peptide synthesis techniques known to a skilled person).

Described herein are methods and related compositions and systems that in some embodiments can be used in the selective detection and quantification of steroids, and in particular, the selective detection and quantification of 17α-ethinylestradiol.

Further characteristics of the present disclosure will become more apparent hereinafter from the following detailed disclosure by way or illustration only with reference to an experimental section.

EXAMPLES

The methods for the selective detection and quantification of 17α-ethinylestradiol and related compositions and systems herein described are further illustrated in the following examples, which are provided by way of illustration and are not intended to be limiting.

Example 1: Synthesis of an
4-Azido-1,8-Naphthalimide-Based Probe 3

In some embodiments, criteria that can be employed in the initial design of the probes described herein can be: 1) The probes absorb and emit in the visible spectral range and in particular possess large Stokes' shifts (e.g., >30 nm) to avoid sample autoluminescence; 2) The probes can be easily assembled and functionalized; 3) The probes can possess a significant and specific response (e.g., fluorescence emission) to the analyte under study (e.g., EE2).

Figure 3:
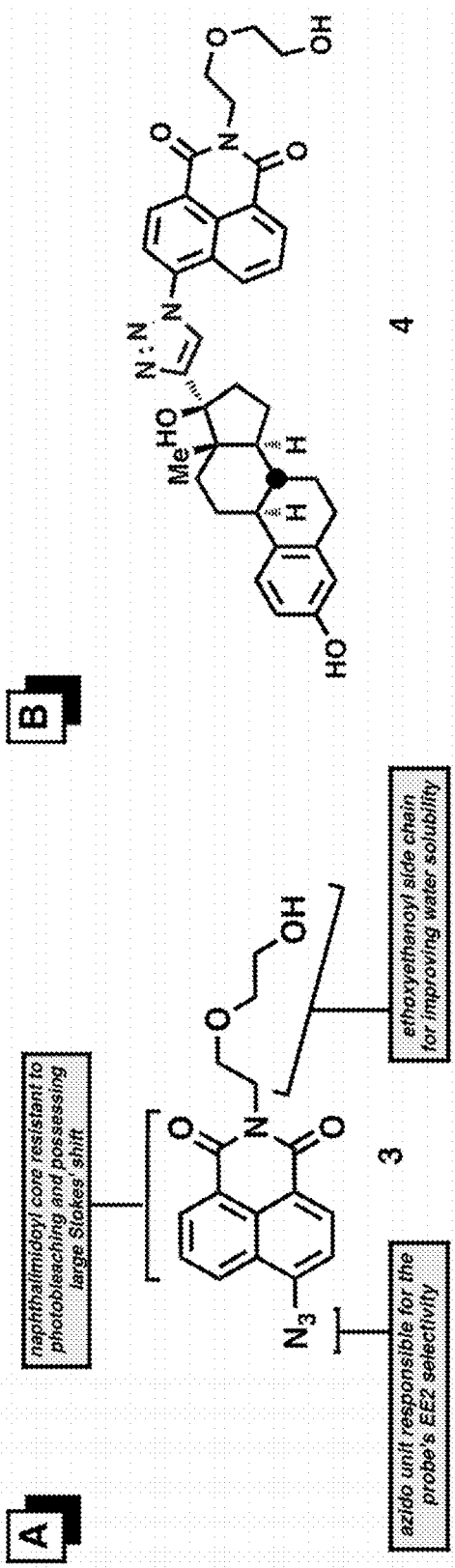
FIG. 3 shows a schematic of a fluorogenic probe and fluorescent triazole adduct according to embodiments herein described.

By way of example, with the three criteria cited above as guidelines for the design of the probe, the naphthalimidoyl-based probe 3 (FIG. 3, panel A) was initially proposed. Probe 3 features a pendant ethoxyethanoyl arm that can improve the probe's water solubility. In addition to increasing the water-solubility properties of 3, the ethoxyethanoyl side arm can provide an opportunity for further chemical modifications in 3 by making use of the free hydroxyl group at its terminus. In addition, the azide functionality at the C4 position of the naphthalimide ring is involved in the Click reaction with EE2 to eventually create the fluorescent product 4 (FIG. 3, panel B).

In addition, there are two other attributes of probe 3. The first one is the fact that only species bearing a terminal alkyne functionality in a given mixture can react in a 1,3-dipolar cycloaddition fashion to yield a fluorescent product (e.g. EE2 adduct 4 in FIG. 3, panel B). A skilled person will recognize that in some embodiments, only terminal alkynes participate in the click reaction, internal alkynes (e.g., those present in drugs such as the antifungal Terbinafine) remain un-reactive during the process. Secondly, is the fact that probe 3 does not emit any fluorescence [Ref 3] by itself but upon covalently binding EE2 forming the triazole product 4, this adduct becomes intensely fluorescent (see, e.g., FIG. 6 in Example 3).

Figure 4:
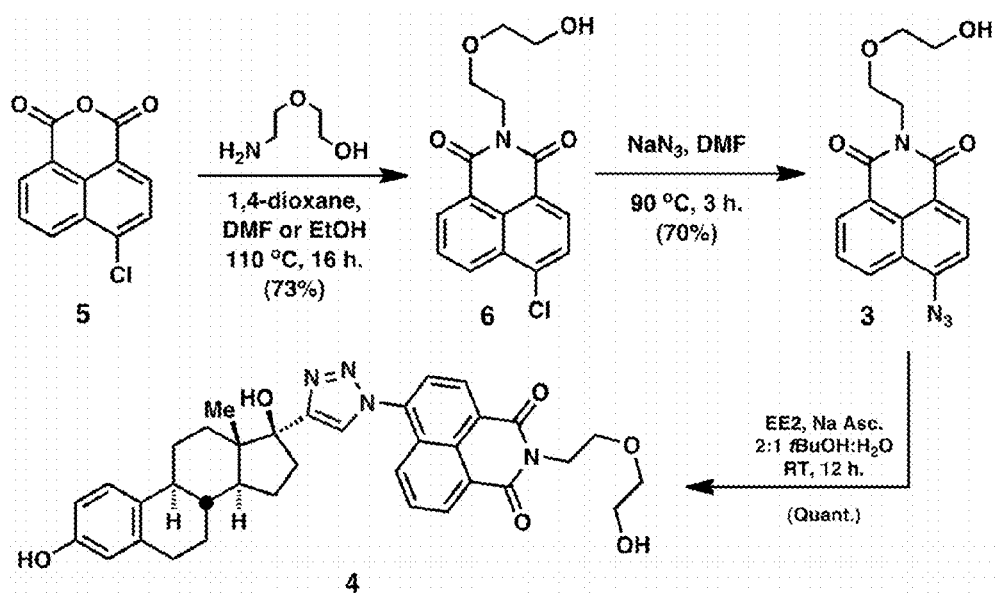
FIG. 4 shows a schematic of an exemplary synthesis of an azido probe according to embodiments herein described and its covalent modification with EE2 using Click chemistry. Probe 3 can be kept in the dark and under refrigeration to avoid any degradation processes leading to the formation of fluorescent by-products. Whereas triazole-containing product 4 does not seem to undergo the degradation pathways that 3 exhibits.

The synthesis of the exemplary naphthalimide probe 3 is outlined in FIG. 4 along with its final conjugation to 17α-ethinylestradiol (EE2) using Click chemistry. The synthesis commences with the condensation of 2-(2-aminoethoxy)ethanol with 4-chloro-1,8-naphthalic anhydride 5 in EtOH, 1,4-dioxane or DMF to afford 4-chloro-1,8-naphthalimide 6 in 73% yield as a fluorescent, yellow oil. Alternatively, the synthesis can also be accomplished using the 4-bromo 1,8-naphthalic anhydride starting material as both of these are commercially available, with the 4-chloro compound 5 being significantly less expensive than its 4-bromo counterpart. Treatment of naphthalimide intermediate 6 with sodium azide in DMF (yields when using anhydrous DMF instead of EtOH were higher 70% vs. 43% respectively) delivered novel, non-fluorescent 4-azido-1,8-naphthalimide compound 3 in 70% yield after purification. Due to the possible degradation of aryl azides through light and thermally catalyzed (heating above 60° C.) pathways this material was kept in an amber glass vial and under refrigeration after its purification via flash column chromatography. Reaction of azido probe 3 with 17α-ethinylestradiol (EE2) in the presence of $CuSO_4.5H_2O$ (10 mol %) and sodium ascorbate (20 mol %) furnished the probe labeled EE2 product (4) in quantitative yield as an off-white solid that readily precipitated from the mixture and was collected by vacuum filtration.

Example 2: Fluorescent Emission Measurements on an EE2-Probe Adduct

Figure 5:
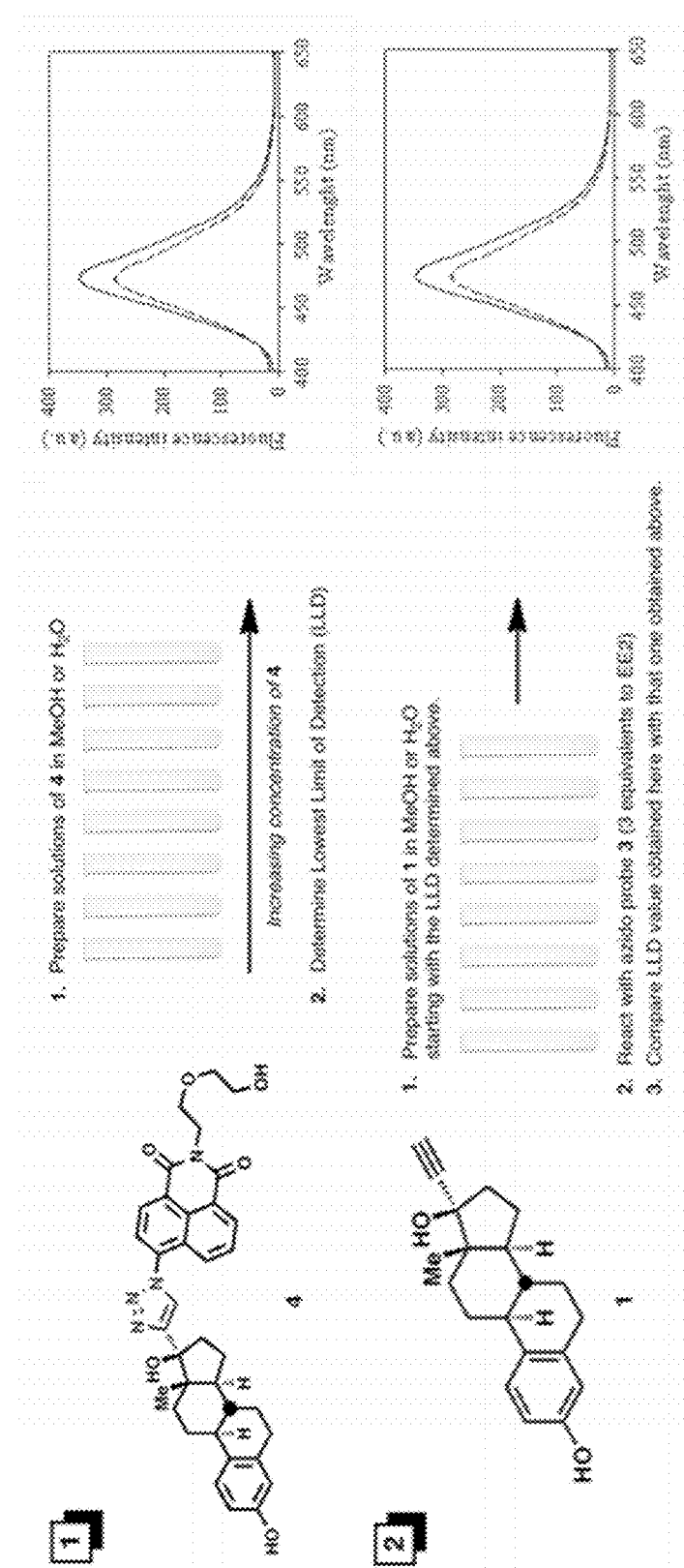
FIG. 5 shows a schematic of an exemplary experimental setup for the fluorescence measurements on an exemplary EE2-probe adduct and an exemplary azido probe.

A feature of the probes herein described is the means by which a readable fluorescent signal can be reliably detected once the azidonaphthalimidoyl probe (see Example 1, compound 3) reacts with EE2. Thus, fluorescent measurements can be conducted on azido probe 3 (Example 1) before and after its reaction with commercially available 17α-ethinylestradiol (EE2, 1) (FIG. 5). Previous studies indicate that the probe 3 does not emit a fluorescent signal and only does so when it reacts with EE2 forming a triazole link at its C4 position. Thus, the fluorescence profile of the EE2-probe adduct 4 can be obtained at different concentrations in order to obtain the lowest limit of detection for this analytical approach (Panel 1 of FIG. 5). Once that lower limit has been determined, a second set of experiments can be undertaken to test the efficacy and fidelity of the Click reaction. In this second experimental setup, different concentrations of EE2 (including the one representing the lowest limit of detection obtained in the first experimental measurements with 4) are reacted with excess azido probe 3 (typically >3 equivalents relative to EE2) under Click chemistry conditions overnight (Panel 2 of FIG. 5). After the overnight run, the samples can be extracted into an organic layer ($CH_2Cl_2$ or diethyl ether), evaporated, redissolved in the solvent of choice for the fluorescence measurements (e.g. $H_2O$, or a combination of MeOH/$H_2O$) and their fluorescent intensities measured. This second set of experiments is designed to test the real case scenario where the actual, unknown EE2 concentration in a given sample can be detected using the azido probe. The outline of this procedure is given in FIG. 5.

Example 3: Testing of an Azido Probe with 17α-ethinylestradiol (EE2)

Figure 6:
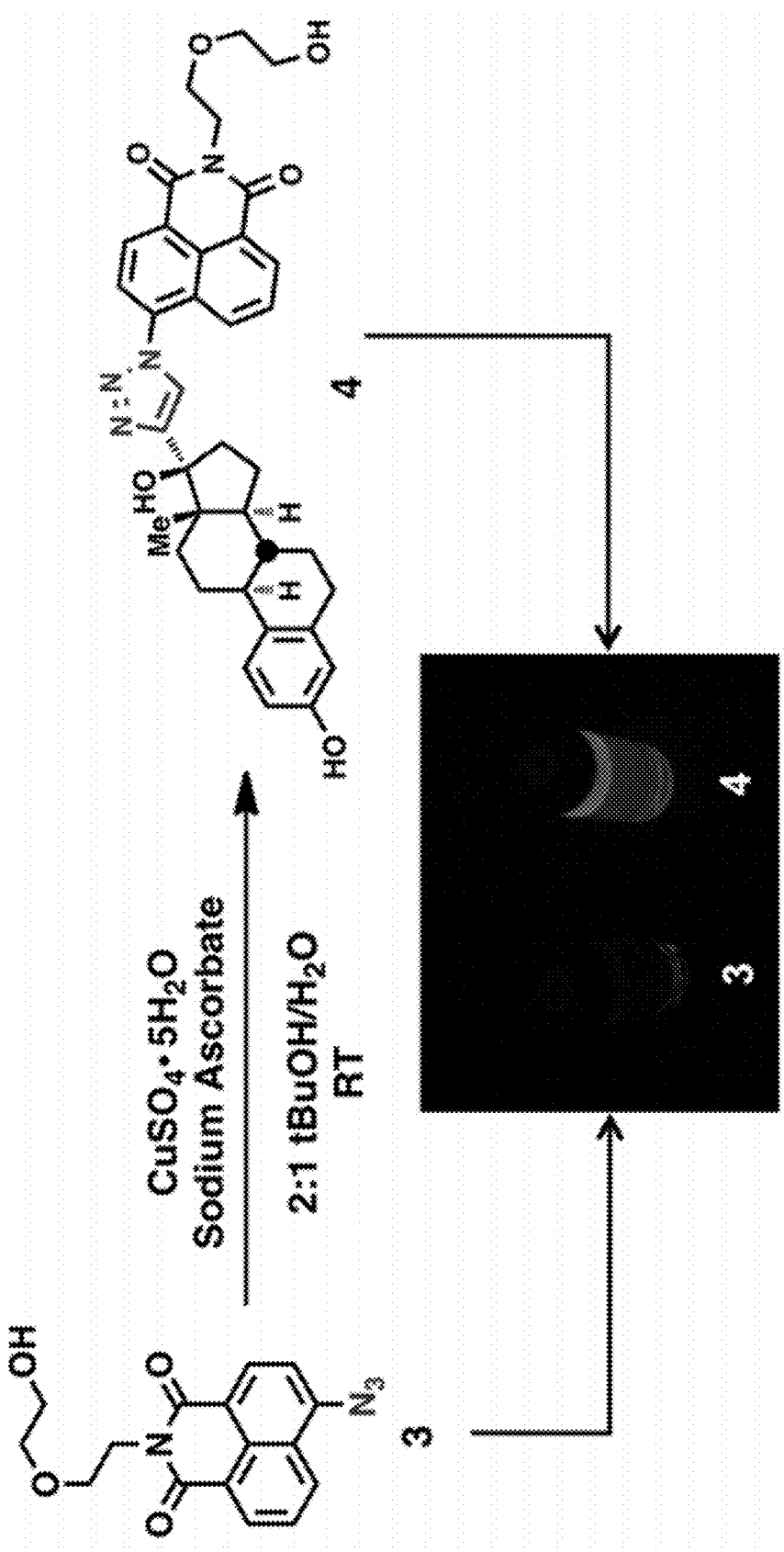
FIG. 6 shows a schematic an photograph of visual fluorescence analysis of an exemplary azido probe and an exemplary EE2-probe adduct according to embodiments herein described. Both vials contain equimolar amounts of the azido probe and EE2-probe adduct respectively. The solution of EE2-probe adduct (4) shows visible fluorescence while the solution of the azido probe (3) does not.

Once an azido probe as herein described (e.g. 3) is synthesized (Example 1), it can be reacted with commercially available EE2. For example, reaction of azido probe 3 with EE2 in the presence of $CuSO_4 \cdot 5H_2O$ and sodium ascorbate in a 2:1 tert-butanol-water mixture at room temperature overnight yielded the triazole-containing EE2-probe adduct 4 in nearly quantitative yield (>95%) as an off-white solid after column chromatography. The use of another source of Cu(I) ion such as CuBr or CuI can be employed in this step, eliminating the need for sodium ascorbate. However, copper(I) halides can be avoided if a reduction in unwanted background fluorescence when using the spectrophotometer is desired. If a cost reduction is desired, instead of copper(I) halides readily available and inexpensive Cu(II) sulfate pentahydrate and sodium ascorbate can be purchased in multigram quantities and used in reactions with EE2. A preliminary fluorescence analysis of both the azido probe 3 and adduct 4 with a UV lamp using the long wavelength detector ($\lambda$=365 nm), shows qualitatively that product 4 is strongly fluorescent in comparison to the azido probe 3 (FIG. 6). Thus, initial measurements on 3 showed that it possesses marginal fluorescence when excited at $\lambda$=319 nm, whereas the EE2-probe 4 shows a 20-fold increase of fluorescence emission centered at $\lambda$=372 nm at the same excitation wavelength. The calculated Stokes' shift based on this preliminary measurements is $\Delta\lambda$=48 nm.

Example 4: Additional Chemical Manipulations on Azido Probes

Figure 7:
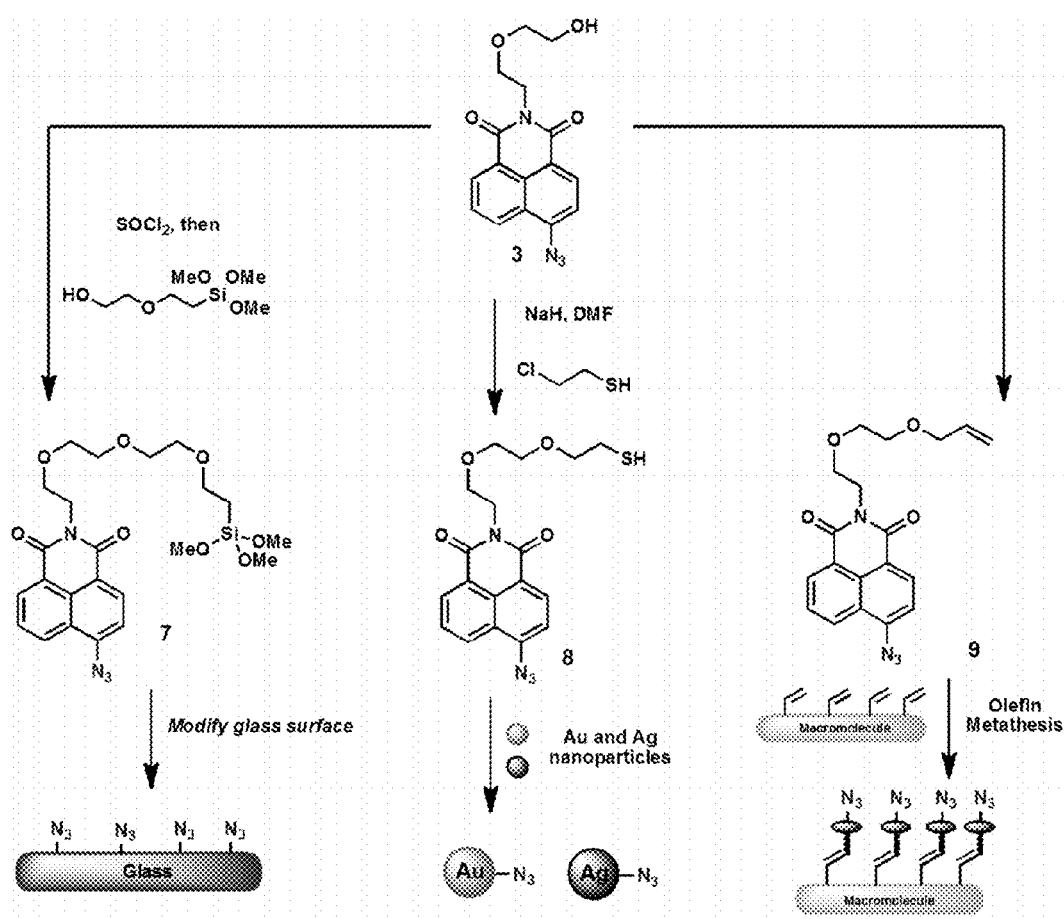
FIG. 7 shows a schematic of exemplary strategies for surface attachment of an exemplary azido probe according to embodiments herein described via chemical manipulation of the terminal hydroxyl group to 1) glass surfaces (left scheme; using siloxane chemistry); 2) Au- or Ag-based nanoparticles (center scheme; using thiol-mediated chemistry) and 3) Olefin-modified macromolecules or surfaces (right scheme; using the Grubbs' Olefin Metathesis).

The nature of azido probe 3 makes it a system that is subject for further elaboration via its chemical modification to achieve desirable physicochemical properties (FIG. 7). A transitory examination of the probe's topology quickly reveals sites at which modifications can be introduced. A skilled person will recognize that in some embodiments, the only site where a modification can be effected without causing any damage to the integrity of the naphthalimidoyl system is the alkyl side arm off the amide nitrogen.

The nature of the amine used in the first step of the synthesis (amine condensation with the 1,8-naphthalic anhydride) can determine the groups can be placed in 3 to strongly modulate its solubility, and to some extent, modulate its fluorescent properties. Thus, there is a library of primary amines than can be used to prepare several analogs of 3 ranging from simple alkyl amines, to more complex, chiral and heterosubstituted amines (such as the (aminoethoxy)ethyl side chain in our prototype probe 3. Furthermore, an amine functionality can be introduced that can be later modified in it via chemical means (as in the case of the hydroxyl group in 3). By way of example, in the case of probe 3, the terminal hydroxyl group can be utilized as a chemical handle to link the dye to a variety of surfaces via its conversion into a siloxy tethered system 7 (for glass surface attachment) or a thiol containing linker such as 8 (for Au/Ag nanoparticles attachment) (FIG. 7). Lastly, modification of the OH group with the allyl group would result in olefin-containing molecule 9 which can be linked to surfaces or macromolecules possessing olefinic group via olefin metathesis (employing, for example, metathesis catalysts such as Grubb's 2nd generation catalysts).

Figure 8:
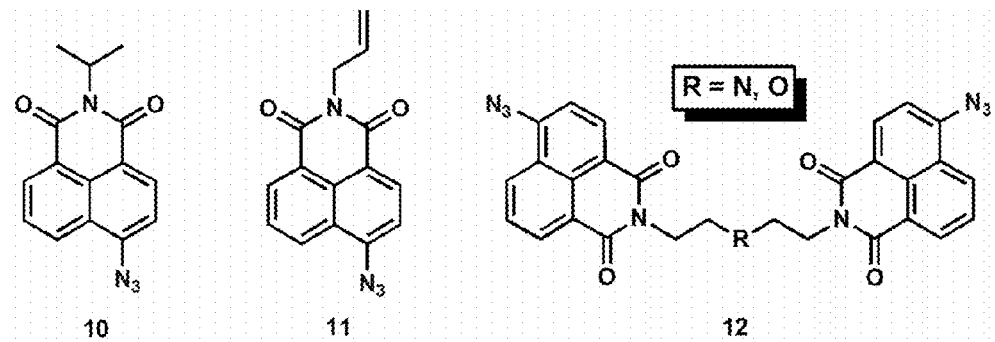
FIG. 8 shows additional exemplary naphthalimides-based probes according to embodiments herein described designed for the detection of EE2 in organic media.

Example 5: Additional Naphthalimide-Based Probes for the Detection of EE2 in Organic Media This Example describes the design of additional probes based on the prototypical azido probe 3 (Examples 1-4). Some of these are shown schematically in FIG. 8. A common structural element among these probes is the 4-azido naphthalimide unit and the only element that distinguishes them from one another is the alkyl group off the amide nitrogen. Thus, probes 10 and 11 possess an isopropyl and an allyl substituent respectively. The presence of these non-polar groups in the probes can render them virtually insoluble in water and as such, their use in organic media is expected to be far superior in detecting EE2 than prototype probe 3. Furthermore, in the case of probe 11, the allyl unit can be used to link this probe to olefin-derivatized surfaces or macromolecules using olefin metathesis protocols (as shown in FIG. 7). Probe 12 is a dimer of the naphthalimide-based system, and it is expected to have stronger detection properties than probe 3 based on the fact that one molecule of 12 can detect two molecules of EE2, thus requiring the use of less probe to obtain an observable signal for the analyte.

Figure 9:
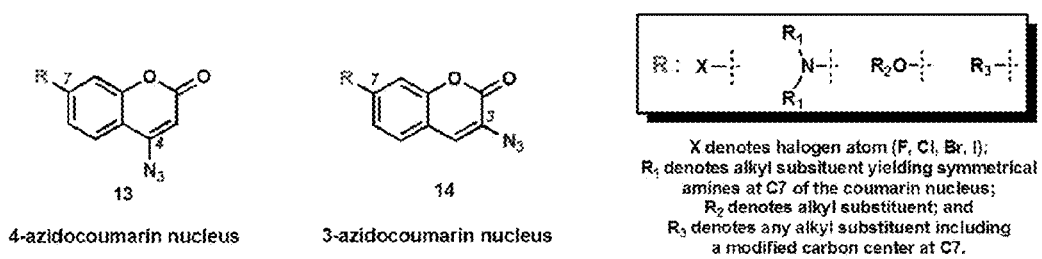
FIG. 9 shows exemplary coumarin-based scaffolds as azido-containing fluorescent probes for EE2 detection. The nature of the R group at C7 of the coumarin nucleus can be used to directly modulate the fluorescent properties of each individual probe.

Example 6: Coumarin-Based Probes: Design, Synthesis and Applications Towards EE2 Detection Fluorescent probes other than the naphthalimidoyl probes with improved physical and spectroscopic properties can also be used in the detection of EE2. Such other probes can include probes with a coumarin scaffold such as, for example, coumarin-based scaffolds 13 and 14 (FIG. 9). Probes 13 and 14 are azido-containing fluorescent probes for EE2 detection in which the nature of the R group at C7 of the coumarin nucleus can be used to directly modulate the fluorescent properties of each individual probe.

Figure 10:
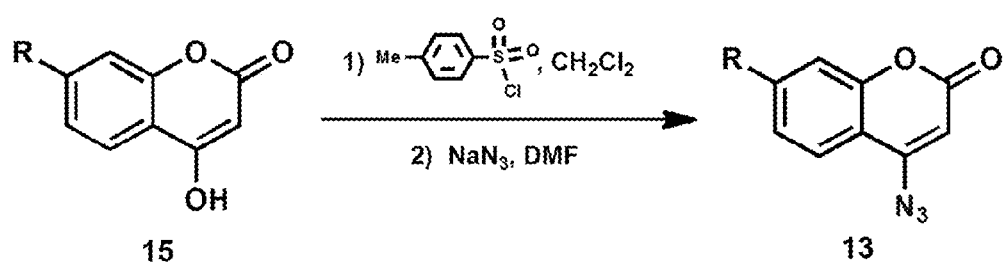
FIG. 10 shows a schematic of an exemplary Synthesis of exemplary 4-azidocoumarin probes according to embodiments herein described.

Two exemplary coumarin scaffolds are ones that differ only in the position at which the azide functionality lies within the heterocyclic system (C4 vs. C3 in FIG. 9). The synthesis of the C4-substituted coumarin analogs can offer a more tractable and concise synthetic pathway than the one posed by their C3 counterparts. The synthesis of the C4-azidocoumarins is outlines in FIG. 10 and it entails the treatment of a commercially available 7-substituted 4-hydroxycoumarin (15) with p-toluenesulfonyl chloride resulting in the activation of the C4 hydroxyl group for nucleophilic displacement which is accomplished with sodium azide in DMF to furnish the C4-azidocoumarin products (13). Likewise, a C4-chlorocoumarin derivative can be used as a starting material instead of its C4-hydroxy counterpart.

Figure 11:
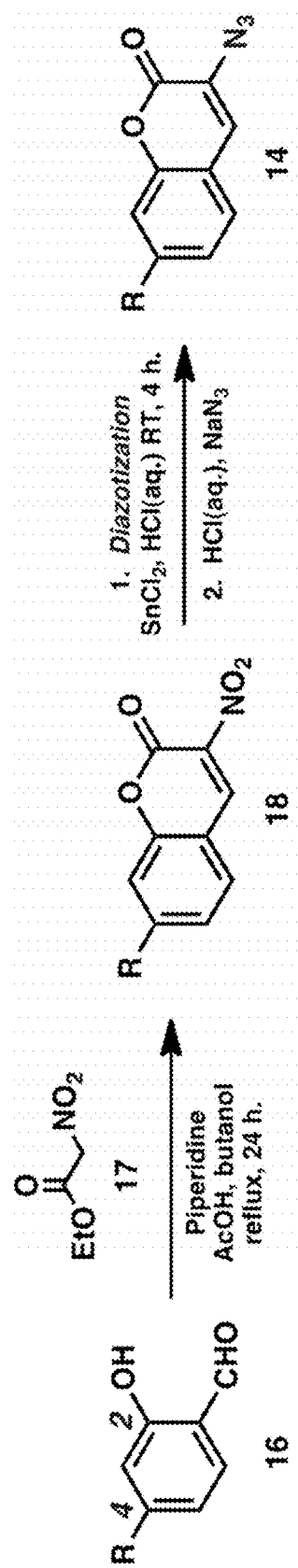
FIG. 11 shows a schematic of an exemplary synthesis of 3-azidocoumarin probes according to embodiments herein described using a diazotization/activation procedure.

The synthesis of the C3-azidocoumarin probes (general structure 14) is outlined in FIG. 11. The synthesis commences with the condensation between a 4-substituted 2-hydroxybenzaldehyde compound (16) with $\alpha$-nitroethyl acetate 17 to generate the C3-nitrocoumarin adduct (18) which undergoes a diazotization reaction followed by nucleophilic displacement with sodium azide to deliver the C3-azidocoumarin product (14). With regards to the use of tin(II) chloride to effect the diazotization reaction in compound 18, more environmentally friendly isopropyl nitrite can be used which does not yield toxic metal by-products (such as Sn).

Figure 12:
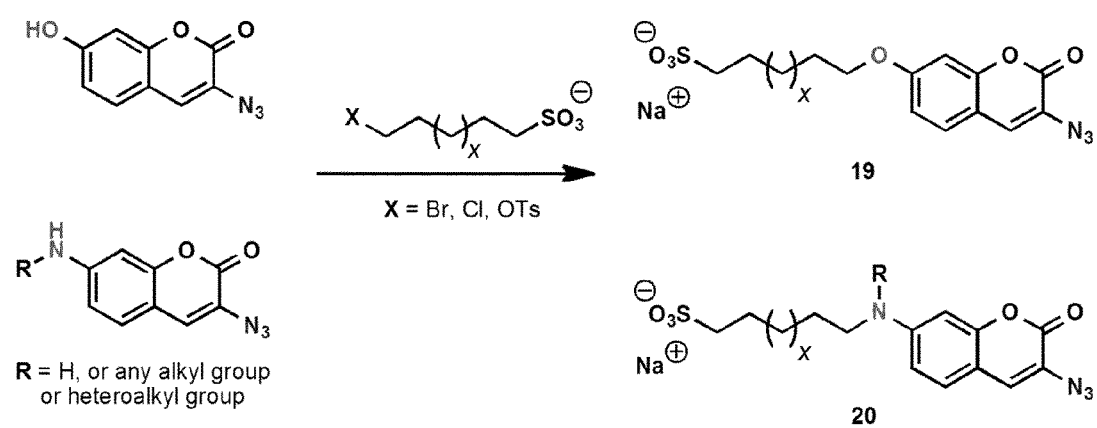
FIG. 12 shows a schematic of exemplary chemical transformations on the C7 R group in coumarin based probes according to embodiments herein described (9 and 10, only showing the manipulations on 10 but the same apply for 9) anticipated to improve the probes' water solubility. The sulfated side arms used in this scheme are commonly used to bestow excellent water solubility of the more non-polar, commercially available carbocyanine infrared probes.
Figure 13:
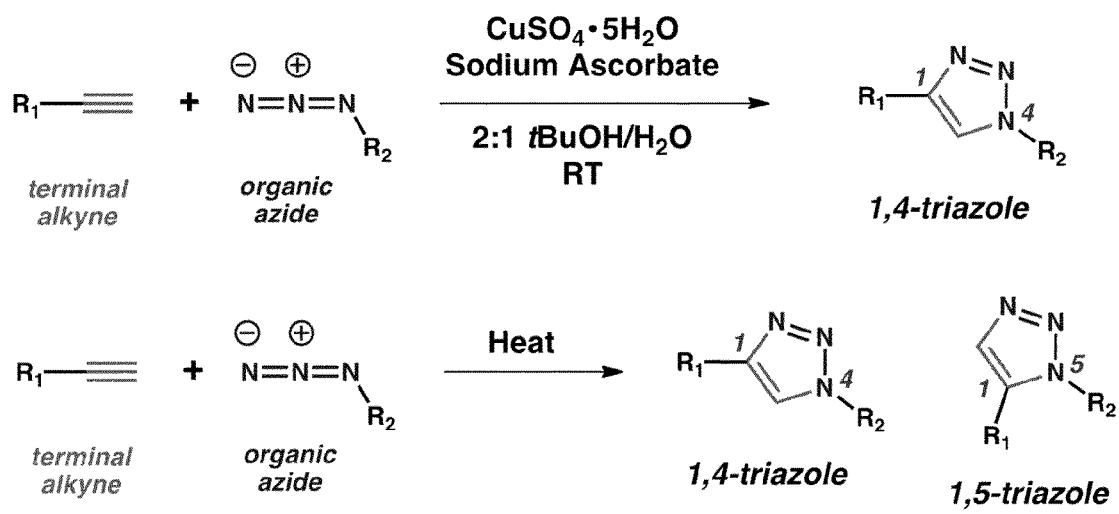
FIG. 13 shows a schematic of the Cu(I)-catalyzed Azide-Alkyne Cycloaddition (CuAAC) reaction to produce a 1,4-substituted triazole ring joining species R1 and R2, whereas the original, thermal addition of the azide and the alkyne yields the 1,5-substituted product in addition to the 1,4-substituted adduct.

Once the syntheses of the coumarin-based probes have been accomplished, their fluorescence properties can be analyzed in an analogous manner to the measurements performed on the naphthalimides probes. Their relative quantum yields ($\Phi_F$) can be determined using, for example, Rhodamine 101 and/or Quinine persulfate, or other dyes known to a skilled person [Ref 6] as possible standards. The nature of the R group in these coumarin-based probes can not only determining the fluorescence profiles of each probe but also can play a key role in rendering the probes water-soluble to some extent. This is an advantage that the naphthalimides-based probes hold over the coumarin-based systems. Thus, the naphthalimidoyl scaffold can be conveniently modified without exactly disrupting the probe's fluorescence efficiency and profile, whereas several chemical manipulations on the coumarin ring would result in a modified core that can show favorable fluorescent properties if groups are attached directly to the aromatic system. These negative attributes that can arise in the coumarin-based systems, can be addressed and solved via chemical transformations designed not to have a detrimental effect on the probe's fluorescent properties. For example, if there is an amine (free or disubstituted) or a hydroxyl group at the C7 position of a coumarin probe, these centers can be alkylated with groups that can enhance the water-solubility properties of the overall probe leaving its fluorescent properties intact (FIG. 12) This approach can be accomplished by using a medium-sized tether (5-6 carbons long) terminating in a free sulfate group (e.g., compounds 19 and 20) The carbon spacer can not only act as a water-solubility improving tether but also it is this tether the entity that does not permit any interactions of the free sulfate at one end to have any effect on the coumarin nucleus. This type of tether has been successfully used in endowing carbocyanine-based infrared probes (IR probes) with excellent water-solubility profiles depending on not only the amount of sulfate-terminated tethers but also on the counterions ($Na^+$ or $K^+$) used in their preparations.

The examples set forth above are provided to give those of ordinary skill in the art a complete disclosure and description of how to make and use the embodiments of the methods for the selective detection of alkyne-presenting molecules and related compositions and systems of the disclosure, and are not intended to limit the scope of what the Applicants regard as their disclosure. Modifications of the above-described modes for carrying out the disclosure can be used by persons of skill in the art, and are intended to be within the scope of the following claims.

The entire disclosure of each document cited (including patents, patent applications, journal articles including related supplemental and/or supporting information sections, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Unless otherwise indicated, the term "alkyl" as used herein refers to a linear, branched, or cyclic saturated hydrocarbon group typically although not necessarily containing 1 to about 15 carbon atoms, or 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 15 carbon atoms. The term "cycloalkyl" intends a cyclic alkyl group, typically having 4 to 8, or 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

Unless otherwise indicated, the term "hydrocarbyl" as used herein refers to any univalent radical, derived from a hydrocarbon, such as, for example, methyl or phenyl. The term "hydrocarbylene" refers to divalent groups formed by removing two hydrogen atoms from a hydrocarbon, the free valencies of which may or may not be engaged in a double bond, typically but not necessarily containing 1 to 20 carbon atoms, in particular 1 to 12 carbon atoms and more particularly 1 to 6 carbon atoms which includes but is not limited to linear cyclic, branched, saturated and unsaturated species, such as alkylene, alkenylene alkynylene and divalent aryl groups, e.g., 1,3-phenylene, —CH2CH2CH2-propane-1,3-diyl, —CH2-methylene, —CH═CH—CH═CH—. The term "hydrocarbyl" as used herein refers to univalent groups formed by removing a hydrogen atom from a hydrocarbon, typically but not necessarily containing 1 to 20 carbon atoms, in particular 1 to 12 carbon atoms and more particularly 1 to 6 carbon atoms, including but not limited to linear cyclic, branched, saturated and unsaturated species, such as univalent alkyl, alkenyl, alkynyl and aryl groups e.g. ethyl and phenyl groups.

Unless otherwise indicated, the term "heteroatom-containing" as in a "heteroatom-containing alky group" refers to a alkyl group in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, and others known to a skilled person, and examples of heteroatom-containing alicyclic groups are pyrrolidino, morpholino, piperazino, piperidino, and other known to a skilled person.

Unless otherwise indicated, the term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

Unless otherwise indicated, the term "alkylamino" as used herein intends an alkyl group bound through a single terminal amine linkage; that is, an "alkylamino" may be represented as —NH-alkyl where alkyl is as defined above. A "lower alkylamino" intends a alkylamino group containing 1 to 6 carbon atoms. The term "dialkylamino" as used herein intends two identical or different bound through a common amine linkage; that is, a "dialkylamino" may be represented as —N(alkyl)2 where alkyl is as defined above. A "lower dialkylamino" intends a alkylamino wherein each alkyl group contains 1 to 6 carbon atoms. Analogously, "alkenylamino", "lower alkenylamino", "alkynylamino", and "lower alkynylamino" respectively refer to an alkenyl, lower alkenyl, alkynyl and lower alkynyl bound through a single terminal amine linkage; and "dialkenylamino", "lower dialkenylamino", "dialkynylamino", "lower dialkynylamino" respectively refer to two identical alkenyl, lower alkenyl, alkynyl and lower alkynyl bound through a common amine linkage. Similarly, "alkenylalkynylamino", "alkenylalkylamino", and "alkynylalkylamino" respectively refer to alkenyl and alkynyl, alkenyl and alkyl, and alkynyl and alkyl groups bound through a common amine linkage.

Unless otherwise indicated, the term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 24 carbon atoms, or aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

Unless otherwise indicated, the term "arene", as used herein, refers to an aromatic ring or multiple aromatic rings that are fused together. Exemplary arenes include, for example, benzene, naphthalene, anthracene, and the like. The term "heteroarene", as used herein, refers to an arene in which one or more of the carbon atoms has been replaced by a heteroatom (e.g. O, N, or S). Exemplary heteroarenes include, for example, indole, benzimidazole, thiophene, benzthiazole, and the like. The terms "substituted arene" and "substituted heteroarene", as used herein, refer to arene and heteroarene molecules in which one or more of the carbons and/or heteroatoms are substituted with substituent groups.

Unless otherwise indicated, the terms "cyclic", "cyclo-", and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

Unless otherwise indicated, the terms "halo", "halogen", and "halide" are used in the conventional sense to refer to a chloro, bromo, fluoro or iodo substituent or ligand.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents.

Examples of such substituents can include, without limitation: functional groups such as halo, hydroxyl, sulfhydryl, C1-C24 alkoxy, C2-C24 alkenyloxy, C2-C24 alkynyloxy, C5-C24 aryloxy, C6-C24 aralkyloxy, C6-C24 alkaryloxy, acyl (including C2-C24 alkylcarbonyl (—CO-alkyl) and C6-C24 arylcarbonyl (—CO-aryl)), acyloxy (—O-acyl, including C2-C24 alkylcarbonyloxy (—O—CO-alkyl) and C6-C24 arylcarbonyloxy (—O—CO-aryl)), C2-C24 alkoxycarbonyl (—(CO)—O-alkyl), C6-C24 aryloxycarbonyl (—(CO)—O-aryl), halocarbonyl (—CO)—X where X is halo), C2-C24 alkylcarbonato (—O—(CO)—O-alkyl), C6-C24 arylcarbonato (—O—(CO)—O-aryl), carboxy (—COOH), carboxylato (COO−), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)2), mono-(C5-C24 aryl)-substituted carbamoyl (—(CO)—NH-aryl), di-(C5-C24 aryl)-substituted carbamoyl (—(CO)—N(C5-C24 aryl)2), di-N—(C1-C24 alkyl), N—(C5-C24 aryl)-substituted carbamoyl, thiocarbamoyl (—(CS)—NH2), mono-(C1-C24 alkyl)-substituted thiocarbamoyl (—(CO)—NH(C1-C24 alkyl)), di-(C1-C24 alkyl)-substituted thiocarbamoyl (—(CO)—N(C1-C24 alkyl)2), mono-(C5-C24 aryl)-substituted thiocarbamoyl (—(CO)—NH-aryl), di-(C5-C24 aryl)-substituted thiocarbamoyl (—(CO)—N(C5-C24 aryl)2), di-N—(C1-C24 alkyl), N—(C5-C24 aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl ((CS)—H), amino (—NH2), mono-(C1-C24 alkyl)-substituted amino, di-(C1-C24 alkyl)-substituted amino, mono-(C5-C24 aryl)-substituted amino, di-(C5-C24 aryl)-substituted amino, C2-C24 alkylamido (—NH—(CO)-alkyl), C6-C24 arylamido (—NH—(CO)-aryl), imino (—CR=NH where R=hydrogen, C1-C24 alkyl, C5-C24 aryl, C6-C24 alkaryl, C6-C24 aralkyl, and others known to a skilled person), C2-C20 alkylimino (CR=N(alkyl), where R=hydrogen, C1-C24 alkyl, C5-C24 aryl, C6-C24 alkaryl, C6-C24 aralkyl, and others known to a skilled person), arylimino (—CR=N(aryl), where R=hydrogen, C1-C20 alkyl, C5-C24 aryl, C6-C24 alkaryl, C6-C24 aralkyl, and others known to a skilled person), nitro (—NO2), nitroso (—NO), sulfo (—SO2-OH), sulfonato (—SO2-O−), C1-C24 alkylsulfanyl (—S-alkyl; also termed "alkylthio"), C5-C24 arylsulfanyl (—S-aryl; also termed "arylthio"), C1-C24 alkylsulfinyl (—(SO)-alkyl), C5-C24 arylsulfinyl (—(SO)-aryl), C1-C24 alkylsulfonyl (—SO2-alkyl), C5-C24 arylsulfonyl (—SO2-aryl), boryl (—BH2), borono (—B(OH)2), boronato (—B(OR)2 where R is alkyl or other hydrocarbyl), phosphono (—P(O)(OH)2), phosphonato (—P(O)(O−)2), phosphinato (—P(O)(O−)), phospho (—PO2), phosphino (—PH2), silyl (—SiR3 wherein R is hydrogen or hydrocarbyl), and silyloxy (—O-silyl); and the hydrocarbyl moieties C1-C24 alkyl (e.g. C1-C12 alkyl and C1-C6 alkyl), C2-C24 alkenyl (e.g. C2-C12 alkenyl and C2-C6 alkenyl), C2-C24 alkynyl (e.g. C2-C12 alkynyl and C2-C6 alkynyl), C5-C24 aryl (e.g. C5-C14 aryl), C6-C24 alkaryl (e.g. C6-C16 alkaryl), and C6-C24 aralkyl (e.g. C6-C16 aralkyl).

Unless otherwise indicated, the term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

Unless otherwise indicated, the term "alkaryl" refers to an aryl group with an alkyl substituent, and the term "aralkyl" refers to an alkyl group with an aryl substituent, wherein "aryl" and "alkyl" are as defined above. In some embodiments, alkaryl and aralkyl groups contain 6 to 24 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Sletten, E. M., et al., "Bioorthogonal chemistry: fishing for selectivity in a sea of functionality." *Angew Chem Int Ed Engl* 2009 48(38): 6974-6998.
2. Prescher, J. A., et al., "Chemical remodelling of cell surfaces in living animals." *Nature* 2004 430(7002): 873-877.
3. Sawa, M., et al., "Glycoproteomic probes for fluorescent imaging of fucosylated glycans in vivo." *Proc Natl Acad Sci USA* 2006 103(33): 12371-12376.
4. Baskin, J. M., et al., "Copper-free click chemistry for dynamic in vivo imaging." *Proc Natl Acad Sci USA* 2007 104(43): 16793-16797.
5. Zhang, L., et al., "Ruthenium-catalyzed cycloaddition of alkynes and organic azides." *J Am Chem Soc* 2005 127 (46): 15998-15999.
6. Horiba, J. Y., "A guide to recording fluorescence quantum yields", 2002, Stanmore.

The invention claimed is:

1. A method for selectively detecting an alkyne-presenting molecule in an untreated sample, the method comprising:
    contacting a detection reagent with the untreated sample for a time and under a condition for click chemistry to allow binding of the detection reagent to the one or more alkyne-presenting molecules possibly present in the untreated sample, the contacting performed in absence of a treatment of the untreated sample that introduces the one or more alkyne-presenting molecules into the untreated sample prior to the contacting;
    wherein the detection reagent comprises an organic label moiety presenting an azide group and wherein binding of the azide group to the alkyne-presenting molecules results in emission of a signal from the organic label moiety.

2. The method of claim 1, wherein the untreated sample is an aqueous or organic solution.

3. The method of claim 1, wherein the organic label moiety comprises a fluorescent or pre-fluorescent moiety.

4. The method of claim 1, wherein the signal is a fluorescent signal.

5. The method of claim 1, wherein the detection reagent has formula I or II:

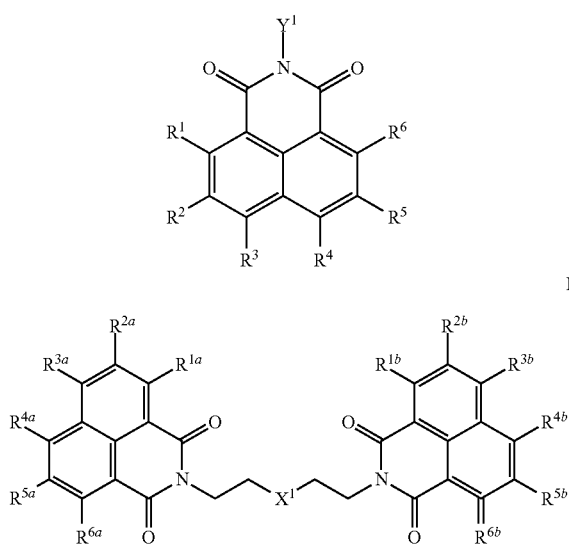

I

II wherein:
- $R^1$-$R^6$ are independently selected from the group consisting of H, $N_3$, substituted or unsubstituted $C_1$-$C_8$ alkyl, substituted or unsubstituted amino such that at least one of $R^1$-$R^6$ is $N_3$;
- $Y^1$ is selected from the group consisting of H, substituted or unsubstituted $C_1$-$C_8$ alkyl, substituted or unsubstituted aryl or heteroaryl, alkoxy, or polyalkoxy;
- $R^{1a}$-$R^{6a}$ and $R^{1b}$-$R^{6b}$ are independently selected from the group consisting of H, $N_3$, substituted or unsubstituted $C_1$-$C_8$ alkyl, substituted or unsubstituted amino, and substituted or unsubstituted oxygen such that at least one of $R^{1a}$-$R^{6a}$ is $N_3$ and at least one of $R^{1b}$-$R^{6b}$ is $N_3$; and
- $X^1$ is O, N, NH, N-alkyl, or N-aryl.

6. The method of claim 5, wherein $Y^1$ is selected from the group consisting of formulas III-VI:

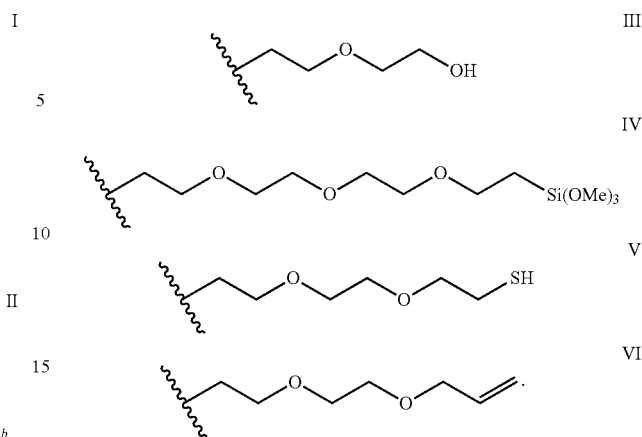

III

IV

V

VI

7. The method of claim 1, wherein the detection reagent has formula VII:

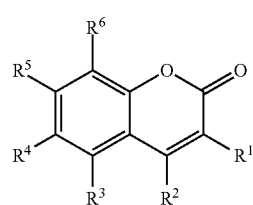

VII wherein:
- $R^1$-$R^6$ are independently selected from the group consisting of H, $N_3$, substituted or unsubstituted $C_1$-$C_8$ alkyl, substituted or unsubstituted amino, and substituted or unsubstituted oxygen such that at least one of $R^1$-$R^6$ is $N_3$.

8. The method of claim 1, wherein the untreated sample is selected from blood, urine, drinking water, and agricultural irrigation water.

* * * * *